United States Patent
Pedley (10) Patent No.: US 10,383,505 B2
(45) Date of Patent: Aug. 20, 2019

(54) LOW COST SENSOR SYSTEM

(71) Applicant: Reckitt Benckiser (Brands) Limited, Slough (GB)

(72) Inventor: Edmund Pedley, Hull (GB)

(73) Assignee: RECKITT BENCKISER (BRANDS) LIMITED, Slough (GB)

(*) Notice: Subject to any disclaimer, the term of this patent is extended or adjusted under 35 U.S.C. 154(b) by 64 days.

(21) Appl. No.: 14/759,211

(22) PCT Filed: Jan. 9, 2014

(86) PCT No.: PCT/GB2014/050051
§ 371 (c)(1),
(2) Date: Jul. 3, 2015

(87) PCT Pub. No.: WO2014/108684
PCT Pub. Date: Jul. 17, 2014

(65) Prior Publication Data
US 2015/0342440 A1 Dec. 3, 2015

(30) Foreign Application Priority Data
Jan. 9, 2013 (GB) .................................. 1300362.9

(51) Int. Cl.
*A47L 15/44* (2006.01)
*G01V 3/08* (2006.01)
(Continued)

(52) U.S. Cl.
CPC ......... *A47L 15/449* (2013.01); *A47L 15/4463* (2013.01); *G01J 5/10* (2013.01);
(Continued)

(58) Field of Classification Search
CPC ........ A47L 15/42; A47L 15/44; A47L 15/449; A47L 15/4463; A47L 15/445;
(Continued)

(56) References Cited

U.S. PATENT DOCUMENTS 3,680,070 A * 7/1972 Nystuen ............... A47L 15/0055
137/5
3,870,417 A * 3/1975 Bashark ............... A47L 15/4297
134/57 D
(Continued)

FOREIGN PATENT DOCUMENTS

WO 2011110243 A1 9/2011

OTHER PUBLICATIONS

International Search Report and Written Opinion from priority PCT Application No. PCT/GB2014/050051, dated Feb. 26, 2014.
(Continued)

*Primary Examiner* — Paul R Durand
*Assistant Examiner* — Andrew P Bainbridge
(74) *Attorney, Agent, or Firm* — Troutman Sanders LLP; Ryan Schneider; Chris Davis (57) ABSTRACT

The invention relates to a low cost sensor array suitable for use in a ware washing machine, preferably a dish washing machine. The invention also relates to a standalone detergent dispensing device comprising the low cost sensor array. The sensor systems are intended to allow monitoring of wash cycles such that controlled sequential dosing of reagents in wash cycles can be optimized. A device comprising such a sensor system may then be able to sense the conditions of the wash and dose reagents in their optimal sequence in the wash.

15 Claims, 4 Drawing Sheets

(51) Int. Cl.
*G01J 5/10* (2006.01)
*G01N 21/84* (2006.01)
*A47L 15/42* (2006.01)

(52) U.S. Cl.
CPC .............. *G01N 21/84* (2013.01); *G01V 3/08* (2013.01); *A47L 15/4287* (2013.01); *A47L 15/4297* (2013.01); *A47L 15/4445* (2013.01); *A47L 2401/06* (2013.01); *A47L 2401/10* (2013.01); *A47L 2401/12* (2013.01); *A47L 2401/26* (2013.01); *G01N 2201/062* (2013.01)

(58) Field of Classification Search
CPC .............. A47L 15/4287; A47L 15/4297; A47L 15/4445; A47L 2401/06; A47L 2401/10; A47L 2401/12; A47L 2401/26; B67D 7/08; D06F 39/00; D06F 39/02; G01N 21/53; G01N 21/85; G01N 21/84; G01N 2201/062; G01N 21/00; G01V 3/08; G01J 5/10
USPC ........... 222/25, 52; 134/18; 73/60.11, 53.01; 700/231; 356/432
See application file for complete search history.

(56) References Cited

U.S. PATENT DOCUMENTS

| | | | | | |
|---|---|---|---|---|---|
| 3,888,269 | A | * | 6/1975 | Bashark | A47L 15/4297 134/113 |
| 4,884,065 | A | * | 11/1989 | Crouse | A61M 5/365 340/632 |
| 5,172,522 | A | * | 12/1992 | Jares | B24B 23/005 16/426 |
| 5,446,531 | A | * | 8/1995 | Boyer | A47L 15/4287 134/113 |
| 5,589,935 | A | * | 12/1996 | Biard | A47L 15/4297 134/113 |
| 5,729,025 | A | * | 3/1998 | Erickson | A47L 15/4297 250/574 |
| 6,567,166 | B2 | * | 5/2003 | Ottens | A47L 15/4297 356/339 |
| 7,180,591 | B1 | * | 2/2007 | Moore | B24B 37/04 356/335 |
| 8,436,292 | B2 | * | 5/2013 | Takahashi | F16C 19/386 250/227.25 |
| 8,631,670 | B2 | * | 1/2014 | Sieglaar | E05B 13/108 70/100 |
| 9,861,255 | B2 | * | 1/2018 | Kim | A47L 15/4214 |
| 2005/0052648 | A1 | * | 3/2005 | Frick | G01J 1/06 356/328 |
| 2007/0034791 | A1 | * | 2/2007 | Sterian | G01J 5/22 250/238 |
| 2010/0175718 | A1 | * | 7/2010 | Kedjierski | A47L 15/4244 134/18 |
| 2011/0030729 | A1 | * | 2/2011 | Gnadinger | A47L 15/0021 134/18 |
| 2011/0139820 | A1 | | 6/2011 | Kessler et al. | |
| 2011/0180118 | A1 | * | 7/2011 | Schrott | A47L 15/0055 134/56 D |
| 2011/0243167 | A1 | * | 10/2011 | Castillo | H01S 5/06804 372/34 |
| 2012/0125366 | A1 | * | 5/2012 | Beshears, Jr. | A47L 15/0047 134/18 |
| 2012/0125384 | A1 | * | 5/2012 | Beshears, Jr. | A47L 15/0047 134/56 D |
| 2012/0222705 | A1 | * | 9/2012 | Steiner | A47L 15/4204 134/18 |
| 2013/0061889 | A1 | * | 3/2013 | Bastigkeit | A47L 15/0055 134/57 D |
| 2013/0092189 | A1 | * | 4/2013 | Tang | A47L 15/4297 134/18 |
| 2013/0278921 | A1 | * | 10/2013 | Choi | G01N 21/85 356/51 |
| 2014/0084024 | A1 | * | 3/2014 | Benda | A47L 15/006 222/113 |
| 2016/0324396 | A1 | * | 11/2016 | Hong | A47L 15/16 |
| 2017/0127905 | A1 | * | 5/2017 | DeWeerd | A47L 15/449 |

OTHER PUBLICATIONS

Combined Search and Examination Report in related GB Application No. GB1300362.9, dated Apr. 19, 2013.

* cited by examiner

LOW COST SENSOR SYSTEM

CROSS-REFERENCE TO RELATED APPLICATIONS

This application is a US National Stage of International Application No. PCT/GB2014/050051, filed 9 Jan. 2014, which claims the benefit of GB 1300362.9, filed 9 Jan. 2013, both which are fully incorporated by reference.

BACKGROUND

In automatic dishwashing machines, the detergent, whether in powder, tablet or gel form, is usually filled manually by the user into the machine, in particular into a detergent holder, before each dishwashing operation.

This filling process is inconvenient, with the problem of exact metering of the detergent and possible spillage thereof, for powder and gel detergents. Even with detergents in tablet form, wherein the problem of accurate dosing is overcome, there is still the necessity of handling the dishwashing detergent every time a dishwashing cycle is started. This is inconvenient because of the usually corrosive nature of dishwasher detergent compositions.

A number of devices are known for holding unit doses of a detergent composition or additive, such as detergent tablets, and for dispensing of such unit doses into a machine.

WO 01/07703 discloses a device for the metered release of a detergent composition or additive into a dishwashing machine having a number of separate sealed chambers for holding the detergent composition or additive and means for piercing the chambers, activated by conditions within the machine.

WO 03/073906 discloses a free standing device for dispensing multiple doses of detergent into a dishwasher. The device has a plate-like construction. A round blister pack, having a plurality of doses arranged around its periphery is loaded into the pack. A winder is then rotated to load mechanical energy into the device sufficient to dispense more than one dose of detergent. A thermally operated latch then moves when the device is subjected to the elevated temperatures within the dishwasher and, in cooperation with a ratchet mechanism, moves the blister pack so that the next dose of detergent is ready for dispensing. In order to dispense the detergent, either the blister pack is pierced, or the dose is ejected from its compartment within the blister pack.

WO 03/073907 discloses a similarly shaped free standing dispensing device. In order to dispense detergent, a lever is manually operated to move a blister pack either to eject the detergent from a compartment within the blister pack, or to pierce the blister pack. A door or flap initially prevents wash liquor within the machine from accessing the exposed detergent. A bi-metallic strip is provided to move the door or flap when the device is exposed to the elevated temperatures during a washing cycle to allow access of the wash liquor to the exposed detergent thereby dispensing the detergent to the machine.

WO2006/021769 relates to an automatic detergent dispensing device that is reactive to temperature changes in the dishwasher.

The prior art devices all react to a simple input from the wash conditions. Normally heat.

WO2005/011462 relates to improved detergent dosing in automatic machine dishwashing. The contents of which are herein incorporated by reference.

This patent discloses the benefits of controlled sequential dosing of treating agents within detergent compositions. The different treating agents within detergent compositions are also often mutually incompatible and interfere with each other, for example the enzymes and the bleach components of most automatic machine cleaning detergents. The controlled sequential dosing is enabled through the use of sensors connected to the washing machine.

BRIEF DESCRIPTION OF THE DRAWINGS

The accompanying Figures, which are incorporated in and constitute a part of this specification, illustrate several aspects described below.

DETAILED DESCRIPTION OF THE INVENTION

It is the object of the present invention to provide a sensor system that would be suitable for use in an automatic washing machine.

Figure 2:
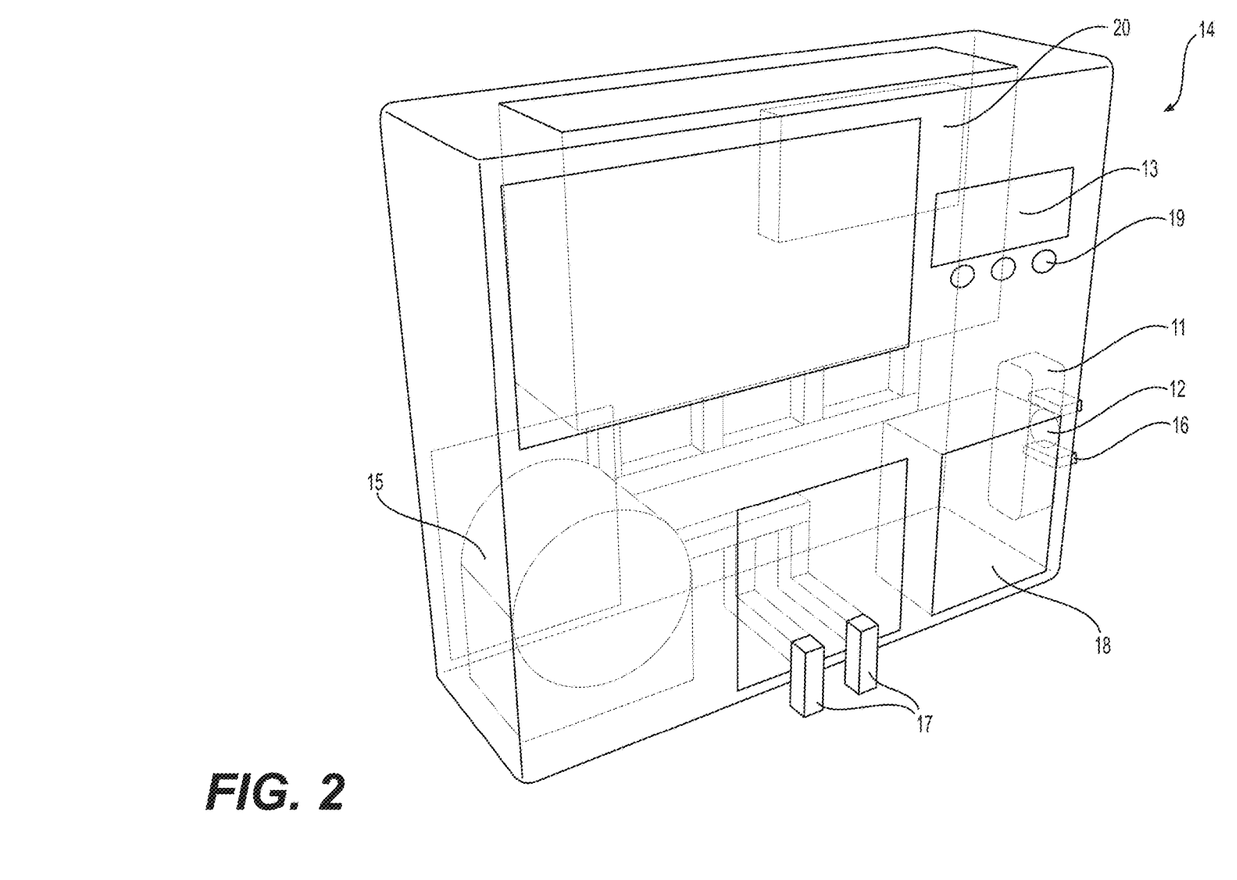
FIG. 2 depicts a front perspective view of an exemplary standalone detergent dispensing device 14, according to some embodiments of the invention, comprising an exemplary sensor system 11 according to some embodiments of the invention.
Figure 3:
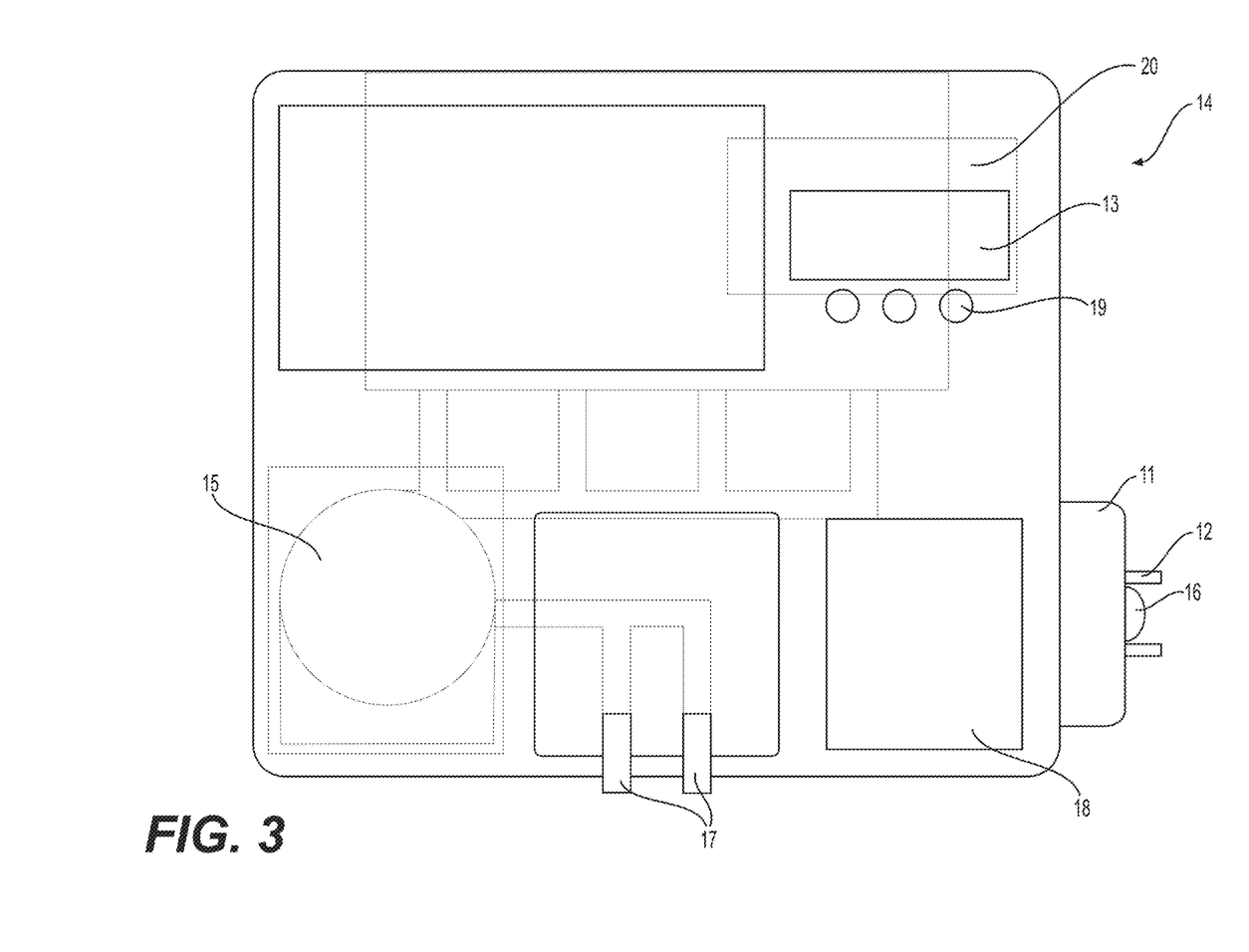
FIG. 3 depicts a front view of an exemplary standalone detergent dispensing device 14, according to some embodiments of the invention, comprising an exemplary sensor system 11 according to some embodiments of the invention.
Figure 4:
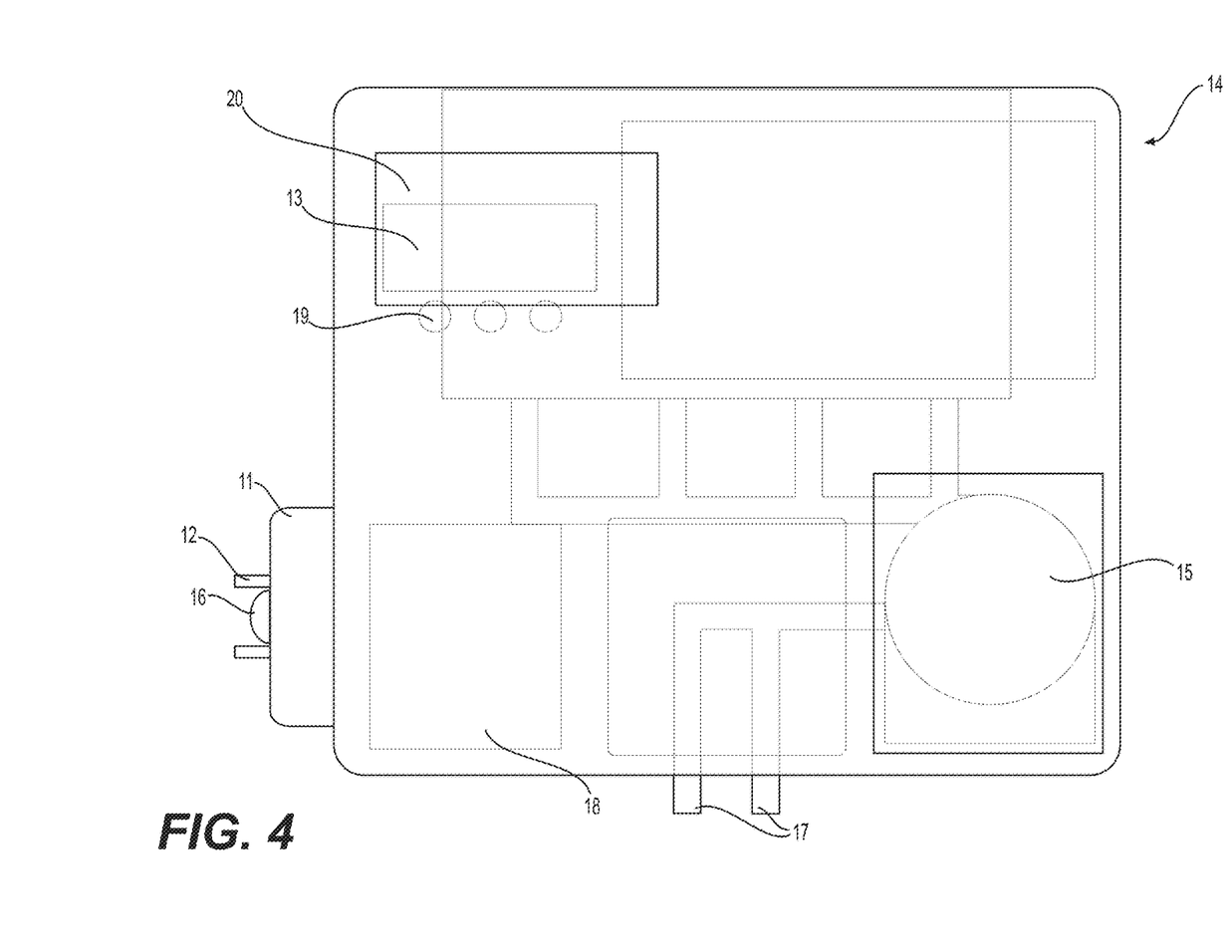
FIG. 4 depicts a rear view of an exemplary standalone detergent dispensing device 14, according to some embodiments of the invention, comprising an exemplary sensor system 11 according to some embodiments of the invention.

In a first aspect of the present invention there is provided a sensor system 11 that is suitable for use inside a ware washing machine that comprises at least one semiconductor 12, preferably a diode.

The present invention is related to the development of sensor systems for use in ware washing machines. The sensor systems are intended to allow monitoring of wash cycles (e.g., by monitor 13) such that controlled sequential dosing (e.g., by controller 19) of reagents in wash cycles can be optimised.

It is preferable that the sensor system is machine independent. By this it is meant that it is preferable that the sensor system can be used in different machines. Therefore it is preferable that the sensor system can correctly interpret wash cycle conditions over a wide range of different wash cycles in different types of machine.

It is the second aspect of the present invention to provide a standalone detergent dispensing device 14 comprising the sensor system 11 of the first aspect of the invention. The device may then be able to sense the conditions of the wash and dose reagents in their optimal sequence in the wash.

In particular the invention relates. It is the object of the present invention to provide a more sensitive device capable of reacting to subtle changes in the wash conditions.

Preferably the device will be able to dose the quantities of the different reagents in response to the sensorial feedback from the sensor system 11 (e.g., the reagents may be dispensed from a dispensing pump 15 or a dosing mechanism 17).

Thus by way of non-limiting example, If turbidity levels are high the detergent dispensing device may release more detergent. To be effective, the device may require software (e.g., in a hardware element 18) to analyse the sensor input and to control the necessary response.

Alternatively it may release set amounts of reagents at specified points in the wash cycle.

Such a device will require a power supply 20. This may be in the form of batteries. Alternatively the device may draw energy from the conditions in the washing machine. These can be heat or motion for example.

Preferably however, the device will use batteries for power.

Because battery power is necessarily limited, sensor power consumption may be important. As will be the mechanism by which the detergent will be dispensed from the device.

For the purposes of the present application any reference to sensor system may apply to the first aspect of the present invention (the sensor system) or to the second aspect of the present invention (a detergent dispensing device comprising the sensor system of the first aspect).

The sensor system 11 needs to be accurate, monitor multiple parameters, be robust enough to survive the conditions of the ware washing machine and be of sufficiently low cost to make it commercially viable.

The sensor system preferably needs to be simple and use the smallest number of sensors to measure the largest number of parameters.

As the sensor system of the present invention is preferably able to work with a standalone detergent dosing device that is capable of being used in a variety of automatic cleaning machines, it must be capable of detecting several different conditions for determining optimal conditions for dosing.

The physical conditions that would be highly desirable to monitor are:
1. Presence or absence of water.
2. Presence or absence of light (to determine if the dishwasher door is open).
3. Water temperature.
4. Rate of change of water temperature.
5. Water turbidity.

The ability to detect the presence or absence of water will allow the sensor system to determine whether or not the machine is currently in a wash cycle or waiting for use.

The ability to detect light and dark will allow the sensor system to determine whether the dishwasher door is open or closed. This will be important for determining whether or not dosing should be carried out.

The ability to detect water temperature and the rate of change of the water temperature will allow the sensor system to determine what stage of the wash cycle has been reached. For example, most wash programs begin with a cool prewash. The sensor array needs to be able to determine this to be able to know when to dose certain ingredients.

Water turbidity is another useful parameter. This is useful to determine whether more reagents need to be added to the wash liquor for an effective clean.

A workable sensor system can be effective that monitors at least three of these parameters. To provide the most sensitive and widely applicable sensor system preferably at least four of these parameters will be monitored and most preferably all five.

Other conditions such as pH level, motion sensing, water hardness etc can also be monitored if desired. These additional sensors may be added to the sensor system of the present invention as desired. The present invention is not limited to the five suggested parameters above.

The sensor system may monitor six or more parameters, preferably seven or more parameters and most preferably eight or more parameters.

At its most simple the present invention would involve the use of a single semiconductor as a sensor system to monitor many conditions within the wash cycle.

The applicants have found that semi-conductor sensors are particularly desirable for use in sensor systems of the present invention.

Semi-conductors are extremely cheap and robust, properties that make them highly effective sensors for the machine cleaning environment.

At its most basic the present invention would involve at least one semiconductor sensor 12 in a sensor system 11.

The preferred type of semi-conductor for the purposes of the present invention are diodes.

The preferred type of diode are LEDs. (Light emitting diodes) The LED may be an infrared light emitting diode.

In a further embodiment the sensor system of the present invention would comprise at least two semiconductor sensors. These may both be forms of diode. Alternatively at least one may be a diode.

In a further embodiment the sensor system of the present invention would also comprise a pair of capacitance plates 16. These can be used to detect when the automatic washing machine is filled with water.

In a further embodiment the capacitance plates 16 could be used as sensors independently of the diode sensors 12. The capacitance plates 16 may be combined with other sensors to provide a different sensor system.

In a further embodiment the sensor system of the present invention may also comprise further sensors. Non-limiting examples may include pH sensors, motion sensors and thermistors. These sensors may be used to add new and different capabilities to the sensor system or improve the performance of previously monitored parameters.

A single semiconductor sensor, preferably a diode, may be able to detect three of the five preferred conditions above. These may be, the presence or absence of light (to determine if the dishwasher door is open), water temperature and rate of change of water temperature.

The diode may be an light emitting diode (LED). The LED may emit light across the frequency band. The LED may emit frequencies outside the visible spectra. In particular infrared emitting diodes are effective.

With an additional semiconductor sensor, which is preferably also a diode, the sensor system may also be able to monitor the water turbidity levels within a ware washing machine (e.g., in conjunction with a monitor 13). The second diode may also be used to provide greater sensitivity to the measurements of light levels and water temperature.

With the addition of capacitance plates 16, the sensor system will be able to detect water presence.

In a preferred embodiment the sensor system would comprise an LED, a photo detector and capacitance plates.

Preferably the LED would be an infrared emitter, the photo detector would be a photodiode or a phototransistor.

| Parameter: | Measured by: |
| --- | --- |
| Water turbidity | Infrared emitter (LED) and infrared detector (photodiode or phototransistor) |
| Water temperature | Same infrared emitter as used for turbidity measurement |

-continued

| Parameter: | Measured by: |
|---|---|
| Ambient light | Same infrared detector as used for turbidity measurement |
| Water presence | Capacitance plates |

This preferred arrangement of sensors would require the use of only two semiconductor sensor components, plus a simple pair of capacitive plates. The capacitive plates even may simply comprise exposed tracking on a circuit board 18 adjacent an external wall of the device.

The preferred sensor system would use a LED to detect temperature. The light detector preferably comprises and phototransistor, (LED or photodiode would also work) and would be used to monitor turbidity and ambient light. Capacitance plates would be preferred to detect water.

This combination would allow enough parameters to be measured for the preparation of the sensor system capable of working with a wide range of different machine types.

Sensors may be internal or external the device. External placement allows for rapid sensing but offers increased risk of leakage into the device. Internal placement allows for protection against the harsh environment of the dishwasher (highly alkaline wash liquor) but may reduce sensitivity, time lag for temperature sensing for example.

A preferred option may be to place the sensors behind a thinned section of the device outer wall. To achieve this the wall can be made of a material that allows transmission of certain wavelengths of light and temperature. For example biaxially orientated polypropylene would allow the transmitence of light sufficient for successful LED and detector sensors. The capacitance plates would also function when placed behind the wall.

Preferably the sensors would be behind an external wall with a thickness no greater than 4 mm, more preferably no greater than 3 mm thick, more preferably no greater than 2 mm thick and most preferably no greater than 1 mm thick.

Treatment Compositions

The device of the present invention may have single treatment compositions to dose. However, preferably the device of the present invention may have two or more different treatment compositions to dose.

More preferably the device would have at least three different compositions, more preferably at least four different treatment compositions and most preferably at least five different treatment compositions to sequentially release.

Non-limiting examples of different treatment compositions that may be included within the device for controlled sequential release may include be a water softening or builder composition, an enzyme composition, a surfactant composition, a bleach composition, a perfume composition, drying or rinse aid composition, or combinations thereof.

The treatment compositions may be in discrete amounts for dosing. The device may dose in multiples of the discrete amount of treatment composition only (e.g., from a dispensing pump 15 or a dosing mechanism 17). Alternatively and preferably the treatment compositions may be metered in controlled amounts (e.g., by a controller 19) according to the output from the sensor system.

The treatment compositions may be in liquid or solid form for metered dosing (e.g., from a dispensing pump 15 or a dosing mechanism 17). The preferred form for the treatment compositions of the present invention are liquids. This is because liquids are easy to measure and dispense and given the high humidity environment inside automatic cleaning machines powdered solids are extremely likely to cake and block dispensers.

EXPERIMENTAL

Measuring Temperature Via a Diode Sensor:

The key parameter of operation of most types of diode (including light-emitting types) which is sensitive to temperature is the forward voltage due to a fixed current. It is this parameter which was examined.

The LEDs were electrically insulated and arranged so that they were connected to a driving circuit using thin wires having a negligible thermal capacity and high thermal resistance. They were then placed in an oil bath having an accurately controlled temperature control system. Precautions were taken to ensure uniformity of temperature distribution throughout the oil bath.

A constant DC forward current of 1 mA was passed through each LED and the forward voltage in each case was examined and recorded for each of a number of oil bath temperatures. The current of 1 mA was selected so as to have a negligible self-heating effect upon the LEDs.

The temperature of the bath was recorded using a thermocouple placed in close proximity to the LEDs. The LED forward voltages and oil temperature was recorded for temperatures of between 37° C. and 100° C. in approximately 0.2° C. intervals.

Figure 1:
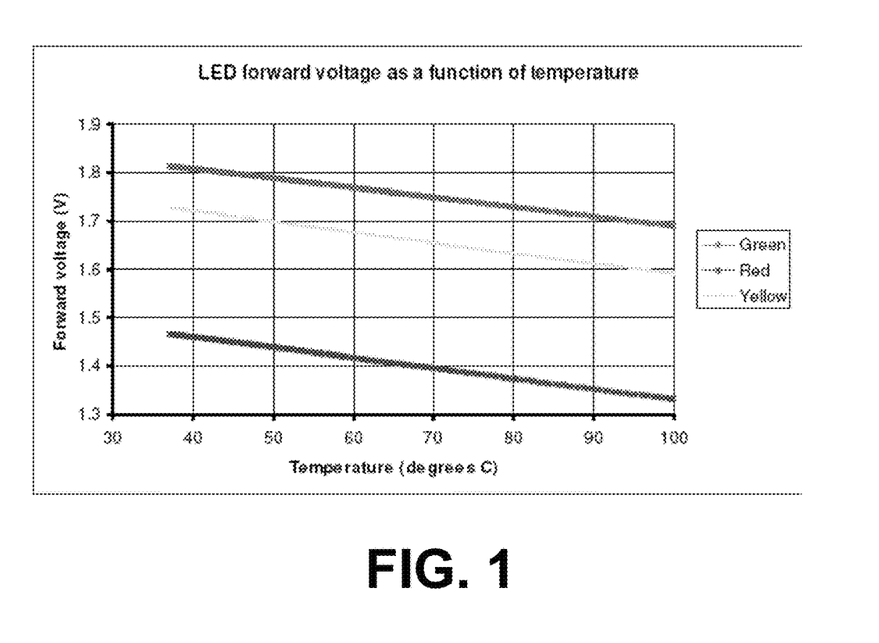
FIG. 1 shows the resulting characteristic of forward voltage against temperature for a typical LED of each of green, red and yellow.

The resulting characteristic of forward voltage against temperature for a typical LED of each colour is shown in FIG. 1.

The observed characteristics of forward voltage are extremely linear, having similar gradients and with differing offsets as would be expected for LEDs of differing colours.

The infrared LED emitter was evaluated in a similar manner to that used for visible LEDs using a fixed forward current of 1 mA and measurement of the forward voltage as temperature is varied. As anticipated a straight line characteristic of forward voltage against temperature was evident which exhibited a gradient of −1.8 mV/° C. and with a voltage value at 25° C. of 0.938V.

This result is broadly similar to those obtained for visible LEDs except for a downward shift in the entire characteristic (approximately from 1.4-1.9 volts to 0.9 volts). This is as anticipated and is characteristic of an LED optimised for infrared operation. The tests have shown that the use of an LED as described results in an extremely linear temperature measurement technique. Thus a single LED can make a highly effective temperature sensor.

Detection of an Ambient Light Threshold Using a LED.

Test were undertaken using samples of each of three randomly selected LEDs, one red, one green and one yellow. These were all general purpose LEDs with conventional 3 mm leaded packages. Because the ambient light measurement is intended to indicate whether the door of the dishwasher is open or closed, two illumination conditions were defined which were representative of the worst-case door-open and door-closed states.

These were as follows:

Door open: Illumination level occurring at the back of the top rack of a dishwasher with the door open and with only relatively poor illumination in the surrounding room. This corresponded to an illumination level of approximately 2 lux.

Door closed: Illumination level occurring anywhere within a dishwasher with the door closed. This corresponded to an illumination level of 0 lux.

The chosen mode of operation of the LED was as a reverse-biased photoconductive device. The alternative photovoltaic configuration was not evaluated because the extremely low voltages generated at the low illumination levels would require the use of a prohibitively expensive circuit configuration.

The LED under test had a reverse bias of 5 volts applied and the resultant reverse current was measured using an Agilent 4329A femto ammeter. This series of tests was performed at an ambient temperature of 20° C. The currents corresponding to the door closed and door open conditions were recorded for each colour of LED and are shown in the table below.

| LED colour | current for each condition: Door closed | Door open | Current ratio (open:closed) |
|---|---|---|---|
| Red | 20 pA | 3 nA | 150:1 |
| Green | 78 pA | 620 pA | 8:1 |
| Yellow | 160 pA | 1.45 nA | 9:1 |

Further tests were undertaken to identify any significant difference in resistance in the Door open condition due to differences in the spectra of ambient light from tungsten or fluorescent light sources. In general terms the red LEDS appeared to be approximately equally sensitive to the two types of lighting whilst the green and yellow LEDs appeared to be approximately 20% less sensitive to tungsten lighting than to fluorescent lighting.

Improved Sensitivity

The infrared phototransistor was evaluated in a similar manner to that used for visible LEDs using the previously defined Door open and Door closed conditions.

The mode of operation of a phototransistor is slightly different from that of a photodiode but still results in a variable current according to the level of illumination. The results obtained at 20° C. are as follows:

| Current for each condition: Door closed | Door open | Current ratio (open:closed) |
|---|---|---|
| <1 nA | 180 μA | 180000:1 |

This result is substantially improved over that obtained with visible LEDs. Although not tested, it is known that the dark current will increase approximately by a factor of 2 for every rise in temperature through an increment of 10° C. Therefore in a worst-case condition of temperature rise of 60° C. (from 20° C. to 80° C.) an increase in Door closed current of 1 nA×26=64 nA. This case would result in a reduced Door open to Door closed current ratio of 2800:1. Again this represents a substantial improvement over the use of visible LEDs.

Water Turbidity

It is quite possible using appropriate circuitry that a conventional optical LED may be used to perform the function of a photodetector—that is as a light detector. It is also possible that an LED may alternate between being used as an emitter and a detector.

The possibility therefore exists that an LED used in the sensor system may serve a secondary purpose as one of the photodetectors which may be required. Perhaps the most obvious area where such a doubling-up of functionality may be achieved is by using a user LED (ie one intended to convey information to the user) as the ambient light detector. However the increased complexity of the circuitry required to implement the dual functionality could conceivably result in an overall cost which is greater than if a separate LED and photodetector were used.

Water Presence—Use of Capacitive Plates

The essence of this technique is to create a variable capacitance formed by a pair of conductive elements housed within the dry conditions in the casework of a sensor system and placed immediately adjacent to the inside wall of the casework. Under conditions of water absence the capacitance between these elements is extremely low. Under conditions of water presence outside the unit, the capacitance between the elements will rise. This is due to the creation of a pair of effective capacitors in series, one between the first element and the water, and the other between the second element and the water.

A simple capacitance-dependent technique was devised which relies upon placing an initial charge upon the capacitor formed by the two conductive elements and then measuring how long the capacitor takes to discharge through a known resistor. This time period indicates the magnitude of the capacitance.

Simple Capacitive Plate Embodiment

A first embodiment consisted of a pair of metal plates each having dimensions of approximately 3 mm×3 mm. These were placed approximately 1 mm apart in contact with the inner surface of an ABS wall section of variable thickness. Tests were undertaken with the outside of this wall being either dry or irrigated with water to a depth of at least 0.5 mm.

The approximate ratios of capacitance of this arrangement between the wet and dry conditions with various thicknesses of ABS wall were as follows:

| ABS thickness | Capacitance wet:dry ratio |
|---|---|
| 0.5 mm | 10:1 |
| 0.8 mm | 5:1 |
| 1.6 mm | 2:1 |

Any increase in depth of water over approximately 0.5 mm resulted in no significant improvement in the capacitance ratio. The use of ABS in these tests was simply due to the availability of suitable sheet material. ABS has a similar but slightly higher relative permittivity than polypropylene and so the capacitance ratios which might be obtained with a polypropylene wall are likely to be broadly similar to those shown above. Because of the high impedance nature of the circuit used in these tests, there was no significant difference in measurements made either using distilled water or sodium chloride solution.

The invention claimed is:

1. A sensor system suitable for use inside a ware washing machine, wherein the sensor system comprises at least one semiconductor wherein one of the at least one semiconductors is a light emitting diode configured to monitor first and second different physical parameters,
    wherein the first physical parameter is wash water temperature, and the second physical parameter is selected from the group consisting of wash water turbidity and light level.

2. The sensor system of claim 1 configured to detect at least four different physical parameters in a ware washing machine.

3. A standalone detergent dispensing device, suitable for use in a ware washing machine, comprising a sensor system comprising at least one semiconductor,
wherein one of the at least one semiconductors is a light emitting diode configured to monitor first and second different physical parameters, and
wherein the first physical parameter is wash water temperature and the second physical parameter is selected from the group consisting of wash water turbidity and light level.

4. The standalone detergent dispensing device according to claim 3 further comprising a power supply and a dispensing apparatus to release treatment compositions in response to inputs from the sensor system.

5. The device according to claim 4, wherein the device has two or more different treatment compositions to release.

6. The device according to claim 4, wherein the device has three or more different treatment compositions to release.

7. The device according to claim 4, wherein the device has four or more different treatment compositions to release.

8. The device according to claim 5, wherein the treatment compositions are selected from the group consisting of enzyme reagents, bleach reagents, surfactant reagents, rinse aids, water softening reagents and mixtures thereof.

9. The device according to claim 5, wherein a dose of each treatment composition can be controlled and metered in response to sensory input from the sensor system.

10. The device according to claim 5, wherein a dose of each reagent is fixed in response to a defined sensory input from the sensor system.

11. The device according to claim 10, wherein the sensor system further comprises a pair of capacitive plates and is configured to detect at least three different physical parameters in the device.

12. A sensor system comprising at least one semiconductor,
wherein one of the at least one semiconductors is a light emitting diode configured to monitor first and second different physical parameters, and
wherein the first physical parameter is temperature and the second physical parameter is selected from the group consisting of turbidity and light level.

13. The sensor system according to claim 1, further comprising wherein the light emitting diode is configured to monitor the additional physical parameter of the rate of change of the wash water temperature.

14. The sensor system according to claim 3, further comprising wherein the light emitting diode is configured to monitor the additional physical parameter of the rate of change of the wash water temperature.

15. The sensor system according to claim 12, further comprising wherein the light emitting diode is configured to monitor the additional physical parameter of the rate of change of the temperature.

* * * * *